United States Patent [19]

Baucke et al.

[11] Patent Number: 5,580,439

[45] Date of Patent: Dec. 3, 1996

[54] REFERENCE ELECTRODE FOR ELECTROCHEMICAL DETERMINATION OF OXYGEN PARTIAL PRESSURE IN AN IONIC MELT

[75] Inventors: Friedrich Baucke, Mainz; Thomas Pfeiffer, Ingelheim; Sylvia Biedenbender, Bingen; Gernot Roth, Dalheim; Ralf-Dieter Werner, Laufersweiler, all of Germany

[73] Assignee: Schott Glaswerke, Mainz, Germany

[21] Appl. No.: 528,949

[22] Filed: Sep. 15, 1995

Related U.S. Application Data

[63] Continuation of Ser. No. 273,009, Jul. 8, 1994, abandoned.

[30] Foreign Application Priority Data

Jul. 24, 1993 [DE] Germany ............... 43 24 922.1

[51] Int. Cl.⁶ ........................................... G01N 27/26
[52] U.S. Cl. ............... 205/782; 205/785.5; 205/786; 204/435; 204/422; 204/423; 204/412; 422/68.1; 422/82.12
[58] Field of Search ............... 204/435, 422, 204/423, 413, 280, 290 R, 291, 292, 412; 422/68.1, 82.12

[56] References Cited

U.S. PATENT DOCUMENTS

| 3,378,478 | 4/1968 | Kolodney et al. | 204/195 |
|---|---|---|---|
| 3,462,353 | 3/1966 | Every et al. | 204/435 |
| 4,007,106 | 2/1977 | Hone et al. | 204/422 |
| 4,313,799 | 2/1982 | Perkins | 204/1 T |

FOREIGN PATENT DOCUMENTS

| 2122758 | 9/1972 | France. |
|---|---|---|
| 2270586 | 12/1975 | France. |
| 2121047 | 4/1971 | Germany. |
| 2749357 | 5/1979 | Germany. |
| 2757985 | 6/1979 | Germany. |
| 2807247 | 8/1979 | Germany. |
| 3507183 | 3/1986 | Germany. |
| 4138409 | 5/1993 | Germany. |

OTHER PUBLICATIONS

Fischer, et al, "Metallurgische Elektrochemie", 1975, pp. 374, 375, 318–326, 244–246 no month available.

Goepel, et al, "Sensors—A Comprehensive Survey", vol. 3, Chemical and Biochemical Sensors part II, 1992, pp. 1156–1180 no month available.

Mueller–Simon, et al, Glastech. Ber. 64 (1991), Nr. 2, pp. 49–51 no month available.

Hladik, "Physics of Electrolytes", vol. 2, 1972, pp. 538–622 no month available.

Samsonov, "The Oxide Handbook", Second Edition, 1982, pp. 44–57 no month available.

*Primary Examiner*—Bruce F. Bell
*Attorney, Agent, or Firm*—Michael J. Striker

[57] ABSTRACT

The method of electrochemical determination of oxygen partial pressure in ionic melts includes providing a metal/metal oxide reference electrode consisting of an electrode body made of a metal selected from the group consisting of Mo, W, Hf, Nb and Ta and alloys thereof and a layer of an oxide of that metal on the electrode body; immersing a pure platinum electrode and the metal/metal oxide reference electrode in a glass melt; measuring a potential across the metal/metal oxide reference electrode and the pure platinum electrode immersed in the glass melt to obtain a measured potential characteristic of the oxygen partial pressure in the glass melt; obtaining a calibration curve relating the potential across said reference electrode and the pure platinum electrode to the oxygen partial pressure in the glass melt as a function of temperature; and obtaining the oxygen partial pressure in the glass melt from the measured potential and the calibration curve. Either the calibration curve is obtained experimentally by immersing a Zirconium dioxide electrode in the glass melt and measuring a potential difference between the metal/metal oxide reference electrode and the Zirconium dioxide electrode at a plurality of temperatures or theoretically from thermodynamic data for the metal/metal oxide reference electrode.

13 Claims, 5 Drawing Sheets

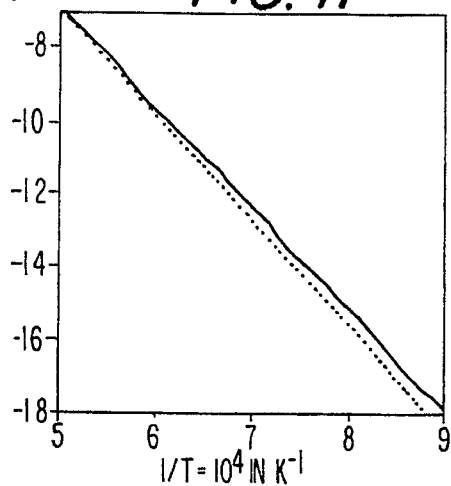
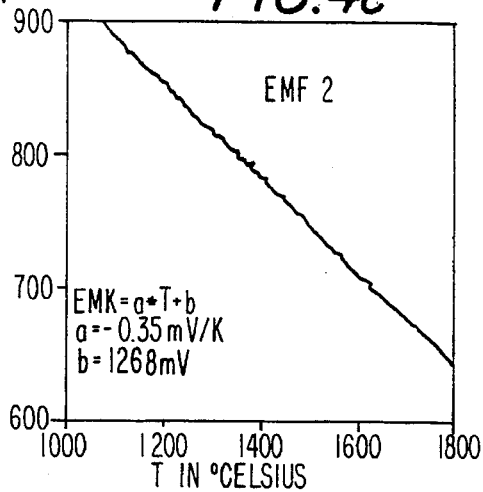
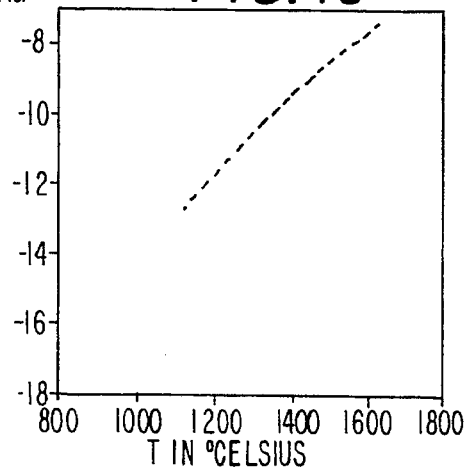
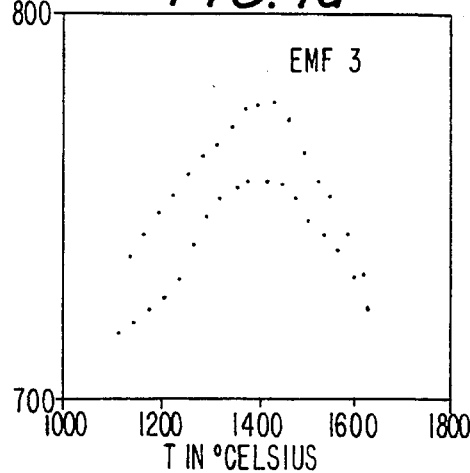
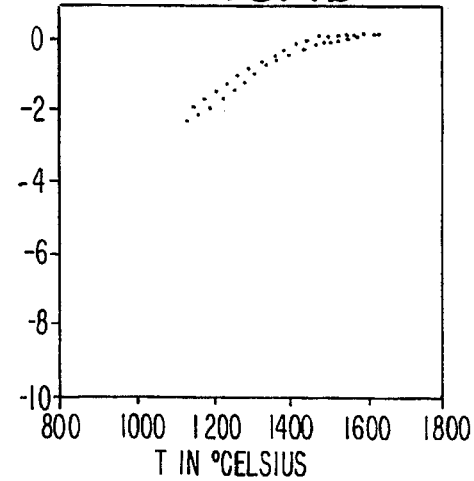
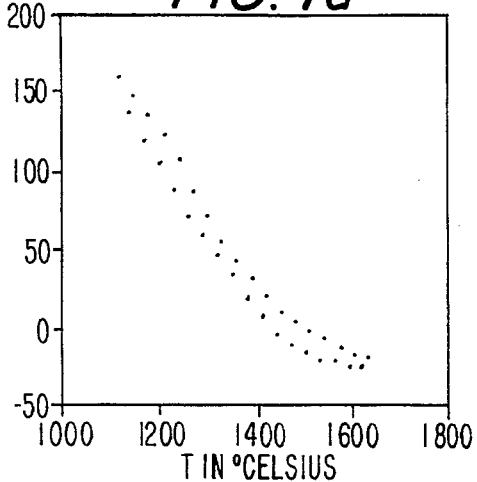

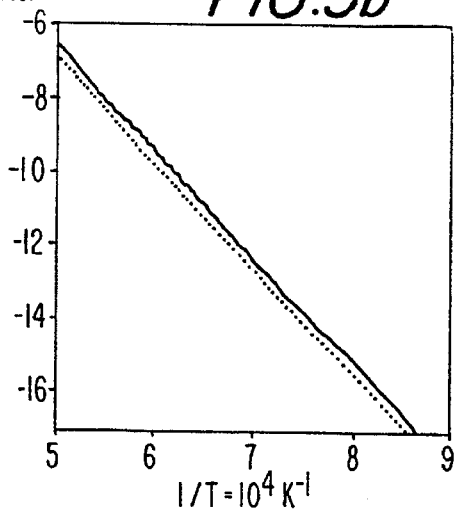
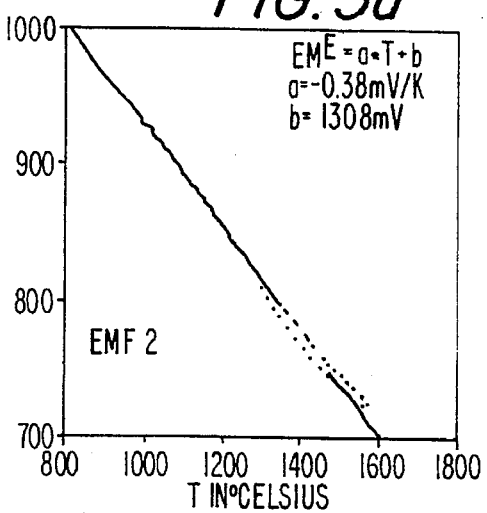
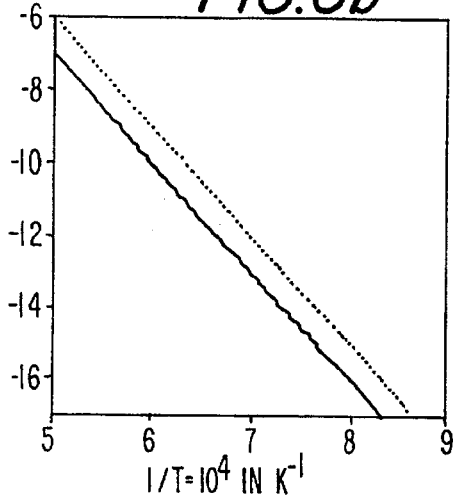
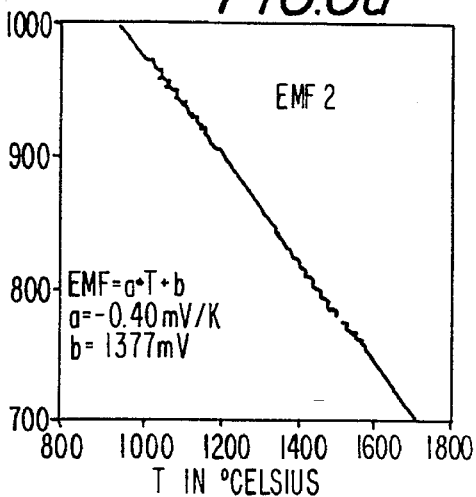
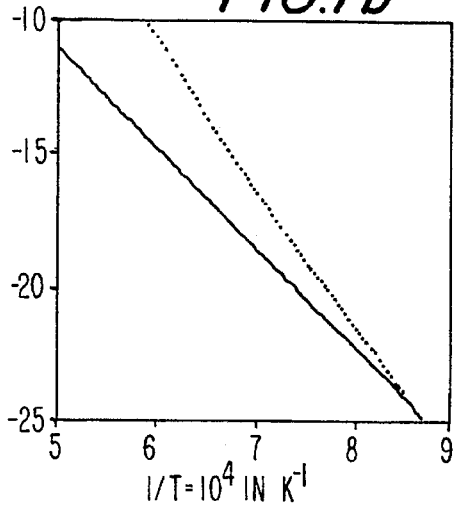
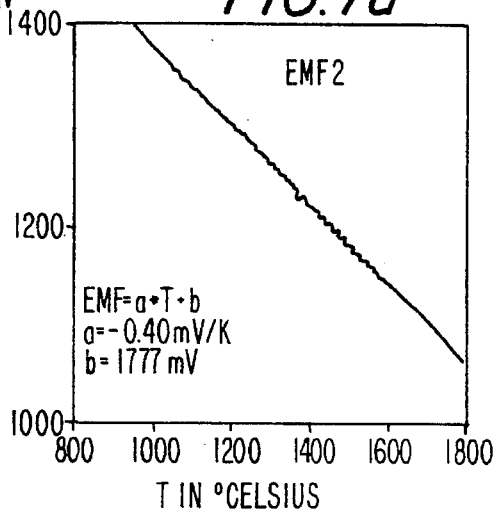

REFERENCE ELECTRODE FOR ELECTROCHEMICAL DETERMINATION OF OXYGEN PARTIAL PRESSURE IN AN IONIC MELT

This application is a continuation of application Ser. No. 08/273,009, filed Jul. 8, 1994 now abandoned.

BACKGROUND OF THE INVENTION

The present invention relates to a reference electrode for electrochemical measurement or determination of the oxygen partial pressure in an ionic melt, especially in oxidic glass melts.

Observation of the quality of glass melts by electrochemical determination of oxygen partial pressure is known. Thus the oxygen partial pressure provides information regarding the redox state of the glass melt. All the properties of the glass melt are effected by the redox state, which can be adjusted or set by the redox system, for example the purity or the color of the melt, in order to name only a few examples. Further details regarding this are provided in, among other references, F. G. K. Baucke, "High-Temperature Sensors for Oxidic Glass-Forming Melts" in Sensors—A Comprehensive Survey; Vol. 3; Chemical and Biochemical Sensors Part II; 1992, pp. 1156–80.

So-called $ZrO_2$-reference electrodes made from yttrium-stabilized Zirconium dioxide have been used up to now for measurement of the oxygen partial pressure, $pO_2$, in glass melts. These known electrodes, on which the claimed invention is based, have been described many times in the technical literature, for example in the above-named prior art reference of Baucke.

The electrochemical cell including its ingredients used to measure the oxygen partial pressure may be represented by

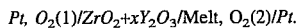

$$Pt, O_2(1)/ZrO_2+xY_2O_3/\text{Melt}, O_2(2)/Pt.$$

The EMF(electromotive force), E, of this electrochemical cell can be used to obtain the partial pressure of oxygen, $pO_2$, in the melt according to the formula (1) below:

$$pO_2(2)=pO_2(1)\cdot\exp(-4EF/RT) \quad (1)$$

where F=Faraday's Constant, R=the gas constant and T=the temperature.

It is essential for the operation of $ZrO_2$-reference electrode that a defined oxygen partial pressure, $pO_2(1)$, exists at the three-phase boundary $Pt(1),O_2(1),ZrO_2+xY_2O_3$. This is most easily guaranteed by a defined gas flow (predominantly air or pure oxygen) or by suitable metal/metal oxide buffer.

A half pipe or a massive cylindrical pin made from Zirconium oxide, which is held by a passage in a cylindrical aluminum oxide pipe, is usually used as the $ZrO_2$-reference electrode. The platinum electrode surrounded by the above-mentioned metal/metal oxide buffer or the oxygen and/or air surrounding atmosphere is located in the interior of the zirconium dioxide pipe and/or ends above the cylindrical massive pin in the aluminum oxide pipe so that contact between the platinum electrode and the zirconium dioxide pipe and/or pin is usually improved by embedding the platinum electrode in a zirconium dioxide powder.

An ideal measurement runs so that exactly 1 mol of oxygen is reacted by "infinitely slow passage" of 4F electrons through the measuring instrument and expands reversibly from higher to lower pressure.

The ceramic Zirconium dioxide in the measurement probe has both a separating and a conducting function. One the one hand it prevents the direct exchange of neutral oxygen and electrons (short circuiting of the cell), and on the other hand it allows the above-described transport of ions (electrolytic key) as an almost pure oxygen ion current. Furthermore Zirconium oxide is in general genuinely stable in regard to corrosion of the glass melt.

These advantages of zirconium oxide have been known for a long time and lead to even more wide usage of it in thermodynamic investigations of solid oxides. The high temperature change stability and corrosion resistance requirements in oxidic glass melts have long prevented their routine use in laboratory glass, especially in fusion by glass furnaces. Problem-free laboratory measurements were possible due to commercial distribution of the Yttrium-stabilized half pipes and rods. Use in glass melt-containing vessels, in which the conditions of usage necessarily require special structure and precautions, has not proven to be so easy. Meantime also a standard solution for this problem does exist (Müller-Simon et.al., Glastech. Ber. 64, 49–51 (1991)).

All available structural forms change nothing regarding the basic weaknesses of the Zirconium dioxide probe: it has a high sensitivity to mechanical and especially thermal stresses. Thus it is difficult to find a suitable mounting location, measurement in melt containers or in pure regions is not practical; and positive results occur only for feed ducts.

A break of the ceramic materials can occur particularly during introduction to a hot melt-containing vessel and/or in retempering or retempering of previously cooled vessels. A breakage or fracture makes the probe ineffective. Broken pieces of ceramics can lead by stone build-up to mechanical blockages in stirring vessels and feed units and to disadvantageous manufacturing stoppages.

Furthermore in a few glass melts the corrosion of the Zirconium oxide is so strong that a reproducible measurement of the $pO_2$ is not possible.

SUMMARY OF THE INVENTION

It is an object of the present invention to provide a reference electrode for electrochemical determination of oxygen partial pressure in ionic melts, especially in oxidic glass melts, which is stable under mechanical and thermal stresses at high temperature and whose suitable installation locations or sites are freely selectable.

According to the invention the reference electrode is a metal/metal oxide electrode. Metal/metal oxide electrodes are known in Electrochemistry of Aqueous Solutions as so-called electrodes of the second kind. They comprise an electrode body made of metal, e.g. a metal rod, which is coated by at least one layer made from a difficult-to-dissolve oxide of this metal. It has been shown that such electrodes are also suitable for measurement in ionic melts, particularly in glass melts.

As in the case of the Zirconium dioxide-reference electrode the determination of the oxygen partial pressure occurs also by measurement of the EMF E of an electrochemical cell. This cell can be represented as follows:

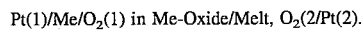

$$Pt(1)/Me/O_2(1) \text{ in Me-Oxide/Melt}, O_2(2/Pt(2).$$

As before the oxygen partial pressure can be calculated using equation (1) but with the oxygen partial pressure $pO_2(1)$ at the metal/metal oxide phase boundary used in place of the oxygen partial pressure $pO_2(1)$ at the Pt electrode. Since one brings a metal Me into equilibrium with its metal oxide $Me_xO_y$ a definite oxygen partial pressure exists at the phase boundary $Me/Me_xO_y$ which still only on depends on the temperature. The thermodynamic behavior of this system is based on the following considerations: that the following reaction is occurring at the $Me/Me_xO_y$ phase boundary $$x\,Me + y\,O = Me_xO_y \tag{2}$$

with the following associated Law of Mass Action $$K(t) = a(Me_xO_y)/(a(Me)^x \cdot a(O)^y) \tag{3}$$

so that no additional chemical degrees of freedom remain. Since the activities in the pure condensed phases, i.e. the metal activity $a(Me)$ and the pure metal oxide activity $a(Me_xO_y)$ according to definition are both 1, the oxygen activity at the phase boundary is determined still only by the temperature dependence of the mass action constant $K(T)$. According to the Laws of Thermodynamics it follows that (see Physical Chemistry Textbooks):

$$\delta log pO_2(Me/Me_xO_y)/\delta(1/T) = -(2/y) \cdot \Delta H°(2.303 \cdot R) \tag{4}$$

where $R$ = gas constant. Accordingly the oxygen activity change with temperature at the $Me_xO_y$ phase boundary is greater the greater the reaction enthalpy, $\Delta H°$. The reaction enthalpy, $\Delta H°$, is only weakly dependent on temperature, otherwise however it is a natural characteristic for a particular metal/metal oxide pair being measured.

On account of simplicity calibration curves for the oxygen partial pressure at the $Me_xO_y$ phase boundary are prepared as a function of temperature. These calibration curves can be used for analysis of the EMF-measurements with the metal/metal oxide electrodes. These calibration curves may be either calculated according to equation 4 from the known thermodynamic data for the concerned metal/metal oxide pair or determined experimentally by measurement of the EMF of the metal/metal oxide electrodes, for example, against a Zirconium dioxide electrode and analysis of the measurement results according to equation 1.

The experimental determination of the calibration curves has the advantage that a characteristic calibration curve can be obtained for each melt. The results of the calibration measurements can be effected by cooperation between special individual components of a melt and the electrode material. The use of a universal calibration curve for the different melts would thus in many cases lead to an incorrect measured oxygen partial pressure.

In contrast these disturbing influences can be eliminated in a simple way by using a characteristic calibration curve associated with each different melt.

This problem cannot be eliminated from the calculation of a theoretical calibration curve according to equation 4. The analysis of the EMF measurements of a metal/metal oxide electrode by such a theoretical calibration curve should thus only be undertaken when only relative values are of interest. A reliable measurement of absolute oxygen partial pressure can not be guaranteed in advance.

For measurement of the oxygen partial pressure in glass melts the electrode according to the invention must comprise a metal, which has a sufficient high temperature resistance to the high temperatures existing in the melts, i.e. has as high a melting point as possible. On the one hand the metal may not be "too noble", so that an oxide layer can be formed (oxide formation thermodynamic criteria), and it should not oxidize too quickly (oxide formation kinetic criteria) in order to guarantee as long a possible lifetime of the measurement probe. Besides the foregoing considerations, factors such as cost, workability, toxicity and so forth, must be considered.

The oxide must similarly have a high melting point and may be difficult-to-dissolve in the glass melt in all cases. The thickness of the oxide layer should advantageously amount to about 10 nm, but it can be sufficient if it amounts to a few atomic layers.

The location, at which the reference partial pressure $pO_2(1)$ is fixed (here the $Me_xO_y$ phase boundary), must be separate from the melt with the partial pressure $pO_2(2)$ to be measured. The requirements regarding the conductivity of ions and electrons in the electrolytic compound were discussed above. $ZrO_2$ fulfills these requirements as a practically speaking pure oxygen ion conductor. In the alternative reference probe the $Me_xO_y$ oxide simultaneously functions as a potential defining substance and also as an electrolytic substance. These requirements are fulfilled when the $Me_xO_y$ oxide is either a pure oxygen ion conductor or also a pure cation conductor (for Me). If it is a mixed conductor, troublesome diffusion potentials can build up, and thus lead to a reduced absolute EMF value. Because of that after a sufficiently long time (e.g. a few hours) stationary, i.e. stable and reproducible, states with respect to diffusion potentials result. The reproducible deviations of the EMF from the theoretical values are taken into account by the calibration.

Furthermore troublesome effects due to chemical reaction between the oxide layer $Me_xO_y$ and the glass melt must be considered. The mixed oxides, the additional solid oxide phases and also the alloys of metals Me with metallic components of the oxide melt must be considered. The disturbing effects can be eliminated as described above in connection with the mixed conductors.

The great advantages of the metal/metal oxide electrodes relative to the conventional $ZrO_2$-probe are their strength and flexibility, since the measurement apparatus does not require any ceramic components. In particular their structure is simpler and they can take greater mechanical and thermal stresses so that they can be easily and safely inserted in a melt-containing vessel. Also the electrodes according to the invention can be used as top electrodes and as side or base electrodes. They can be used both in the melt and also in the purifying vessel. Thus for example the oxygen partial pressure is measurable along the melt-containing vessel shaft in the melt.

The place of insertion of the Pt-measurement electrode commonly used as the counter electrode is determined by the problems to be overcome on insertion of the $Me/Me_xO_y$ electrodes. It must be assumed that there is only a homogeneously melted melt between the place of insertion of the reference and measurement electrodes. The effects of temperature differences on the EMF formation between both electrodes can be corrected with the help of the Standard-Seebeck Coefficients of the glass melt, which can be determined previously in the laboratory experimentally. Thermo- and Diffusion potentials can be corrected also in the same way in a manner which is known in itself (see in this case, e.g., K. S. Goto, W. Pluschkell, "Oxygen Concentration Cells" in: Physics of Electrolytes, Vol. II (Ed. Hladik), London 1972). For evaluation of the $pO_2$ measurement with the $Me/Me_xO_y/Pt$ measurement cell the three variables temperature of the $Me/Me_xO_y$—electrode, temperature of the Pt electrode and the EMF between both these electrode must be continuously received and processed.

Besides it is provided that the very small thermocouple voltages in the vicinity of the electrodes are converted with a voltage/current converter into a current signal and the measured EMF similarly is converted with an impedance transformer in the vicinity of the electrodes and subsequently with a current/voltage converter into a current signal. The current signal of 0 to 20 mA thus produced can then be supplied without difficulty over a wide range to a plant computer or an auxiliary microprocessor, where it can then be processed and stored.

The following metals are particularly suitable for the reference electrode: Hf, Nb, Ta, Mo and W. They all have a high melting point and all form solid oxides with widely differing melting points.

The melting points of these metals and their oxides can be summarized as follows(from The Oxide Handbook, Ed. G. V. Samsonov, New York, 1982):

TABLE I

METAL AND METAL OXIDE MELTING POINTS

| Metal or Metal Oxide | Melting Point, °C. |
| --- | --- |
| Hf | 2150 |
| $HfO_2$ | 2777 |
| Nb | 2468 |
| NbO | >1900 |
| $NbO_2$ | >1900 |
| $Nb_2O_5$ | 1511 |
| Ta | 2996 |
| $Ta_2O_5$ | 1877 |
| Mo | 2610 |
| $MoO_2$ | 1927 |
| $MoO_3$ | 795 |
| W | 3410 |
| $WO_2$ | 1570 |
| $WO_3$ | 1270 |

Thermodynamic data is available for the above-named metals and their oxides which allows the theoretical oxygen partial pressure to be calculated at the $Me/Me_xO_y$ phase boundary according to equation 4. The free energies of formation of some of the above-named metal oxides are summarized as follows in Table II.

TABLE II

METAL OXIDE FREE ENERGY OF FORMATION, $-\Delta G°$, kcal/mol
(Source: The oxide Handbook 1982(see above))

| T = | 1000° K. | 1200° K. | 1400° K. | 1600° K. | 1800° K. |
| --- | --- | --- | --- | --- | --- |
| $HfO_2$ | 920 | 884 | 848 | 814 | 779 |
| NbO | 318 | — | — | 276 | — |
| $Ta_2O_5$ | 1607 | 1523 | 1443 | 1364 | — |
| $MoO_2$ | 389 | — | — | 318 | — |
| $WO_2$ | 401 | 366 | 333 | — | — |

The alloys of the above mentioned metals and their mixed oxides can also be used. Furthermore it is also conceivable that in some applications the above-named metal is doped with another heavy metal.

Besides the metals Ru, Re, Os are also suitable but it is not very advantageous to use them because of the high material and processing costs and in the case of Os because of the high vapor pressure of the toxic oxide.

For the sake of simplicity the oxide layer on the metal electrode body is first formed on immersing the electrode in the melt. Thus one is able to eliminate one manufacturing step for the electrode thus saving processing work. In this case one must only wait prior to the beginning of the measurement until the system comes to equilibrium, i.e. until stable conditions occur.

In the normal case the oxide layer on the electrode dipped in the melt grows further into the metal body. On the other side if the metal oxide is an only difficult-to-dissolve metal oxide, the metal oxide is worn off or eroded from the outside by the melt. This process limits the lifetime of the electrode according to the invention, and it generally leads first to interference with the measurement, when the metal core has nearly completely disappeared. A change of the relative thickness of the metal layer and the metal oxide layer leads to no impairment of the measurement results. For the sake of reliability it is recommended however to test its operation toward the end of the lifetime of the metal/metal oxide electrode by repeated calibration measurements.

The reference electrodes advantageously are made from Mo in a preferred embodiment of the invention. The action of the molybdenum electrode is based on the formation of a thin strongly adherent $MoO_2$ in common glass melts at temperatures of up to about 1900° C. The layer acts simultaneously to passivate the electrode and prevents the rapid corrosion of the comparatively noninert Molybdenum in the glass melt. This is also the same reason that the Molybdenum electrodes can be used as heating electrodes. As illustrated in the subsequent examples, Mo has proven to be outstanding as an electrode material in various glass melts.

Molybdenum rods of the quality usually used for heating electrodes can be used in the electrode according to the invention. Particularly the reference electrode either can be a previously mounted heating electrode disconnected from the heating circuit or an additionally mounted electrode, whose temperature is either measured by a thermocouple electrode in the electrode interior or by an additionally applied thermocouple element. The temperatures of the Mo-electrode portion dipped in the melt should be as uniform as possible. It must also be guaranteed in the Mo-electrode that it is mounted ground-free on the melt container. "Ground-free" means that the electrode is insulated from all portions of the melt-containing vessel.

The electrode is advantageously in the form of a rod or a pipe closed at one end, since it is easily held in this case and can be easily exchanged as needed.

BRIEF DESCRIPTION OF THE DRAWING

The objects, features and advantages of the present invention will now be illustrated in more detail by the following detailed description, reference being made to the accompanying drawing in which:

FIG. 3b is a graphical illustration showing the relationship of the oxygen partial pressure to the temperature as calculated from the experimental data of FIG. 3a;

FIG. 3d is a graphical illustration of the electrode potential EMF3 obtained as a difference EMF3=EMF2−EMF1 from the experimental data for FIGS. 3c and 3a;

FIGS. 4a and 4b are graphical illustrations of the dependence of the electrode potential EMF1 and the oxygen partial pressure, respectively, in an Na-Ca-Silicate glass melt on the temperature as determined using a ZrO$_2$ reference electrode (Pt versus ZrO$_2$);

FIGS. 4c–4f are graphical illustrations of dependence of EMF2 on temperature, of EMF3 on temperature, of oxygen partial pressure on temperature and of oxygen partial pressure on the reciprocal of the temperature, respectively, for a Mo/MoO$_2$ reference electrode (Mo versus ZrO$_2$);

FIGS. 5a and 5b are graphical illustrations showing the dependence of the EMF2 on T and the oxygen partial pressure on 1/T, respectively, in a melt of borosilicate glass 3.3 as determined using a Mo/MoO$_2$ electrode (measuring Mo against ZrO$_2$);

FIGS. 6a and 6b are graphical illustrations showing the dependence of the EMF2 on T and the oxygen partial pressure on 1/T, respectively, in a melt made from the same borosilicate glass as in FIGS. 5a and 5b as determined using a W/WO$_2$ electrode (measuring W against ZrO$_2$); and FIGS. 7a and 7b are graphical illustrations showing the dependence of the EMF2 on T and the oxygen partial pressure on 1/T, respectively, in a melt made from the same borosilicate glass as in FIGS. 5a and 5b as determined using a Ta/TaO$_2$ electrode (measuring Ta against ZrO$_2$).

DESCRIPTION OF THE PREFERRED EMBODIMENTS

1. Measurement Apparatus

Figure 1:
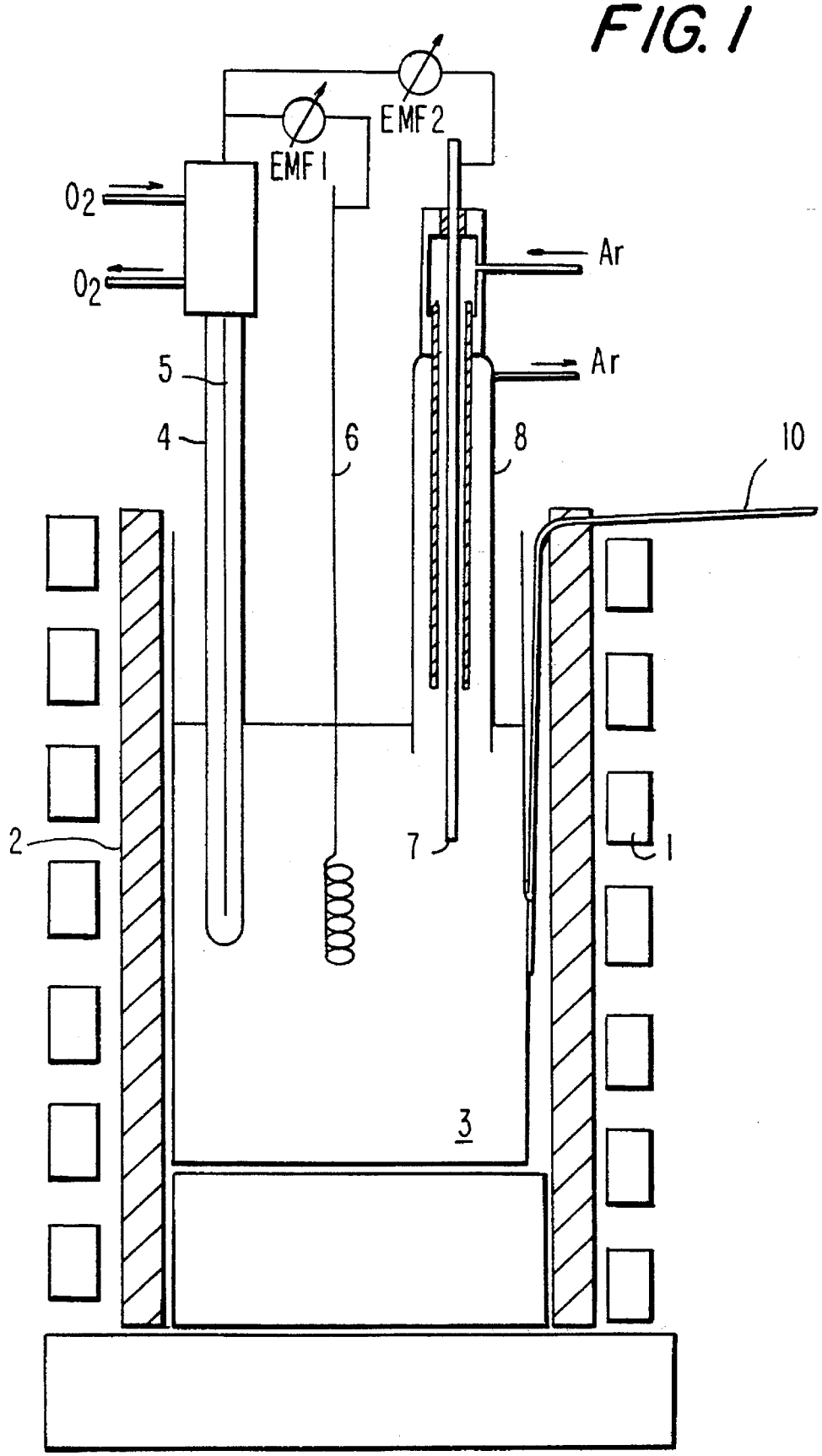
FIG. 1 is a schematic cross-sectional view of a measurement apparatus for making a calibration curve for a metal/metal oxide electrode according to the invention.

The operation of the alternative reference electrodes was tested in a series of technical glass melts. The calibration curves shown in the drawing result particularly from measurement of the EMF of the metal/metal oxide electrode against a conventional Zirconium dioxide electrode as a function of temperature. These calibration curves and/or the thermodynamic data derived from them were compared to theoretical data and/or calculated curves for the concerned metal/metal oxide pair for confirmation of the utility of the alternative reference electrodes of the invention.

The experimental apparatus for producing the calibration curves is shown in FIG. 1. Three electrodes 4,6,7 were inserted from above in a glass melt 3 which is heatable by an induction coil 1 in a platinum vessel 2. These three electrodes 4,6,7 include a conventional ZrO$_2$ electrode 4 with a Pt-interior conductor 5 and an interior oxygen rinse (at 1 bar); a pure platinum electrode 6 and a metal/metal oxide electrode 7 according to the invention. The metal/metal oxide electrode 7 is a Mo, Ta or W rod of a diameter of about 4 mm and length of 400 mm whose portion which is not immersed in the glass melt is advantageously protected under an inert gas atmosphere, e.g. Ar, inside a sleeve 8 which surrounds that portion of electrode 7 which is outside of the glass melt.

The metals used had the following purity:

Mo: 99.95% 0.03% W (Metallwerk Plansee, Reutte (I))

Ta: 99.90% 0.04% Nb (Metallwerk Plansee, Reutte(I))

W: 99.96% 0.01% Mo (Metallwerk Plansee, Reutte (I))

Voltages between the electrodes 4,6,7 were measured. The temperature of the melt was measured with the help of a thermocouple element 10. The oxygen partial pressure present in the glass melt is obtained in the standard way using equation (1) hereinabove from the EMF 1 measured across electrodes 4 and 6 as indicated in FIG. 1. The oxygen partial pressure at the metal electrode or the Me$_x$O$_y$ phase boundary is also calculated from the EMF 2 from equation (1).

The testing events consisted in subjecting the glass melt provided with the electrodes 4,6,7 to a definite temperature program with standard temperature cycles. The temperatures were varied at between 40 K/h and 400 K/h over a temperature range several hundred degrees. In several experimental cycles the melts were stirred additionally mechanically (stirring devices are not shown here).

2. Measurement Analysis Methods

The measurement apparatus in FIG. 1 provides the measured variable EMF (Pt/ZrO$_2$)=EMF 1 and EMF (Me/ZrO$_2$)=EMF 2 for the metals Me=Mo, W or Ta as a function of temperature.

Figure 3F:
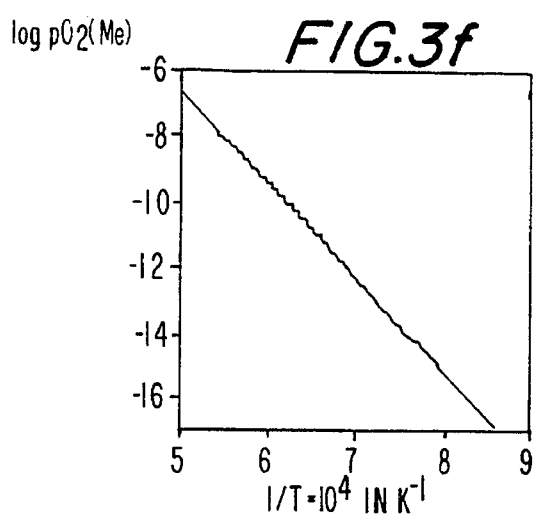
FIG. 3e and 3f are graphical illustrations of the dependence of oxygen partial pressure at the phase boundary Me/Me$_x$O$_y$ on T and 1/T, respectively, as derived using EMF3.
Figure 3C:
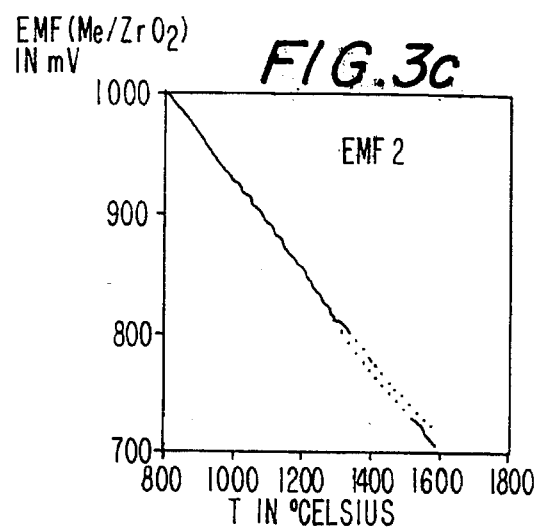
FIG. 3c is a graphical illustration of the dependence of electrode potential EMF2 on temperature as measured using a metal electrode versus $ZrO_2$.
Figure 3E:
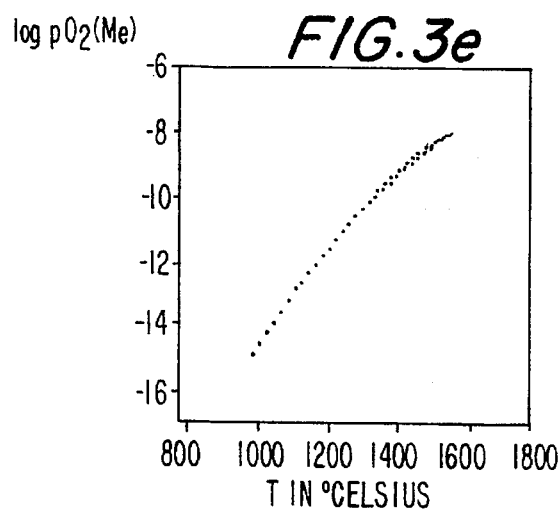
Figure 3D:
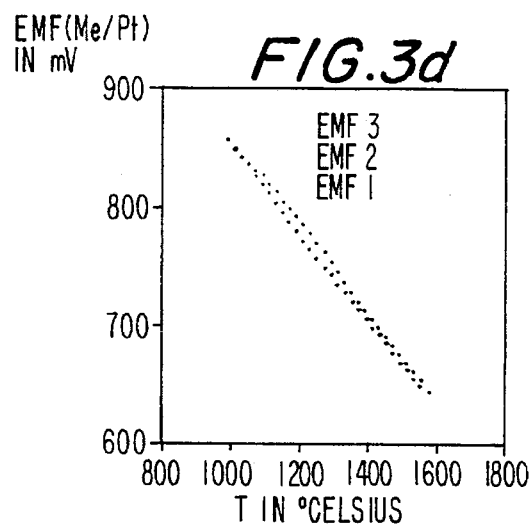
Figure 3B:
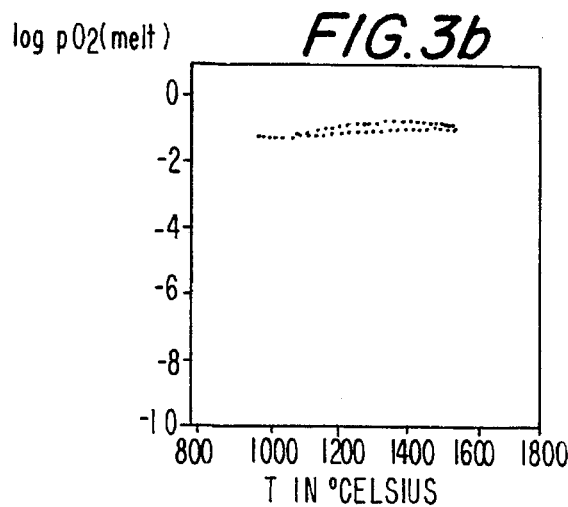
Figure 3A:
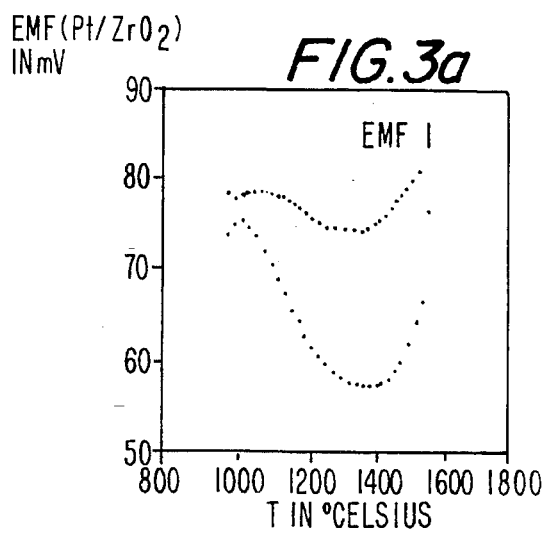
FIG. 3a is a graphical illustration of the dependence of the measured electrode potential EMF1 on temperature obtained by using a $ZrO_2$ reference electrode(Pt versus $ZrO_2$)

The typical measurement results and their analysis for one melt are shown in FIGS. 3a to 3f. The dependence of EMF1 and EMF2 is shown in FIGS. 3a and 3c respectively. FIG. 3b shows the oxygen partial pressure calculated from the data for FIG. 3a using equation (1). The similarly produced EMF (Me/Pt)=EMF 3 is obtained as a difference EMF 3=EMF 2–EMF 1. The values of EMF3 so determined appear as a function of temperature in FIG. 3d. The reverse way would be adopted in practice in glass furnace uses of the electrochemical cell Me/Me-oxide/melt, pO$_2$/Pt. The individual "calibration curves" EMF2=f(T) of the metal Me for the particular melt serve as a basis for the calculated conversion EMF3—EMF1—pO$_2$ (melt). Both EMF2=f(T) and pO$_2$ (Me/MexOy)=f(T) can be used as calibration curves. Only different mathematical formulations of the problem are required.

Exactly as one calculates a momentary and local oxygen partial pressure of the melt from the EMF 1 (see equation 1 and FIG. 3b as an example of the analysis for pO$_2$ in the glass melt with the conventional "ZrO$_2$-probe") one obtains a numerical value for the oxygen partial pressure at the phase boundary Me/Me-oxide.

Two functional dependencies of the oxygen partial pressure at this phase boundary are contrasted with each other in FIG. 3: namely, log pO$_2$ versus T, temperature, in FIG. 3e and log pO$_2$ versus 1/T in FIG. 3f. From these results one can derive the thermodynamic data of the oxidation reaction at the phase boundary Me/Me$_x$O$_y$. One obtains the reaction enthalpy from the following formula (5) by rearranging equation (4) above:

$$\Delta H° = \{\delta \log pO_2(Me/Me_2O_y)/\delta(1/T)\} \cdot (2.303 \cdot R \cdot y/2) \quad (5)$$

The reaction entropy is most easily calculated using the following formula (6):

$$\Delta S° = \{\delta EMF(Me/ZrO_2)/\delta T\} \cdot (4 \cdot F) \quad (6)$$

The curves should like the thermodynamic variables be characteristic of the metal, otherwise however they should be independent of the choice of the glass melt. Deviations are observed on comparison of a measured curve with a theoretical curve which is based alone on the thermodynamic data for the corresponding oxidation reaction between the pure components. The theoretical curves are indicated with dashed lines in the first graph in the following figures.

As long as variations from the theoretical curves remain reproducible for all types of glass, as mentioned above, an empirical calibration curve can be used.

3. Reference Electrode made from Mo/MoO$_2$ in Technical Glass Melts

The results determined from FIGS. 4a to 4f and 5a and 5b were obtained in tests of molybdenum in melts of different technical glasses. The graphical illustrations show the results for a series of experiments, in which temperature cycles with different heating and/or cooling speeds, were performed in part with simultaneous stirring. A pure metal bar was used whose oxidized layer was first formed on dipping in the glass melt.

In all experiments one finds a good to very good agreement of the theoretical and experimental values. It is also to be noted that the temperatures used in the analysis were determined to an accuracy of at most 10° C. The individual variations could moreover be based on the formation of different "doped" MoO$_2$ layers and different diffusion potentials in the layers and melt.

All Mo-bars have a silvery, partially yellowish, shimmering, solid layer at the end of the tests independent of the type of glass being used. The thickness of this layer is in the vicinity of micrometers after at least a few weeks use.

Sufficiently reproducible calibration curves may be obtained for all glass melts. Usually without particular limitation the functional relationship, EMF 2=f(T), was selected as calibration curve. The first time adjustment time of the probes is within a few hours of glass contact. Higher temperatures accelerate the stabilization of the measured EMF. After that the probes were ready for use. In particular: Soda Lime Glass (Composition: SiO$_2$ 74% by weight; CaO 10% by weight; Na$_2$O 16% by weight; Sb$_2$O$_3$ 0.2% by weight): After several weeks use no problem occurs with the probes. The glass contains antimony which however does not have any negative effects.

Borosilicate glass 3.3 (ISO 3585v.07/91): The molybdenum rod shows the least corrosion traces in the NaCl refined Borosilicate glass melt. The pO$_2$ of the melt varies as expected only a little with temperature.

The experimental thermodynamic data and the coefficients a and b of the "calibration curves" from the measurements are compared to the theoretical values of the solid body reaction Mo+O$_2$=MoO$_2$ (from the Oxide Handbook, vide supra) in the following Table III. The comparison of the data supports the conjecture that a MoO$_2$ layer forms in the glass melt analyzed here. The results also coincide with earlier observations reported in the Literature.

TABLE III

| | Comparison of Experimental and Theoretical Data for Mo/MoO$_2$ | | | | | |
|---|---|---|---|---|---|---|
| | ΔH° exp kJ/mol | ΔH° theo kJ/mol | ΔS° exp J/K | ΔS° theo J/K | −a mV/K | b mV |
| Soda Lime Glass | −525 | −553 | −140 | −140 | 0.35 | 1268 |
| Borosilicte Glass | −545 | −553 | −152 | −140 | 0.38 | 1308 |

Reference electrodes were made from W/WO$_2$ and Ta/Ta$_2$O$_5$ in a Borosilicate glass melt (Borosilicate glass 3.3). Reference electrodes made of the metals Tungsten and Tantalum were also tested as alternatives to Molybdenum. The first survey-type tests were limited to reactions in the above-described Borosilicate glass melt. The results of the measurements are generally positive for these metals as shown in FIGS. 6a, 6b and 7a, 7b (in these examples the results are produced with the aid only of the calibration curves EMF 2=f(T); the additional curves shown in FIGS. 3a–f and 4a–f may be easily calculated with the help of the EMF 1 measurements, as described above). The analogous theoretical curves determined for the Mo-reference electrodes which were indicated with dashed lines for comparison in the drawing correspond to that. Table IV provides a comparison between the experimentally measured thermodynamic data obtained according to equations 5 and 6 from the measurement results and the theoretical values:

TABLE IV

| | Comparison of Experimental and Theoretical Data for W/WO$_2$ and Ta/Ta$_2$O$_5$: | | | | | |
|---|---|---|---|---|---|---|
| Electrode | ΔH° exp kJ/mol | ΔH° theo kJ/mol | ΔS° theo J/K | ΔS° theo J/K | −a mV/K | b mV |
| W/WO$_2$ | −570 | −572 | −160 | −170 | 0.40 | 1377 |
| Ta/Ta$_2$O$_5$ | −1795 | −2027 | −400 | −420 | 0.40 | 1777 |

Figure 2:
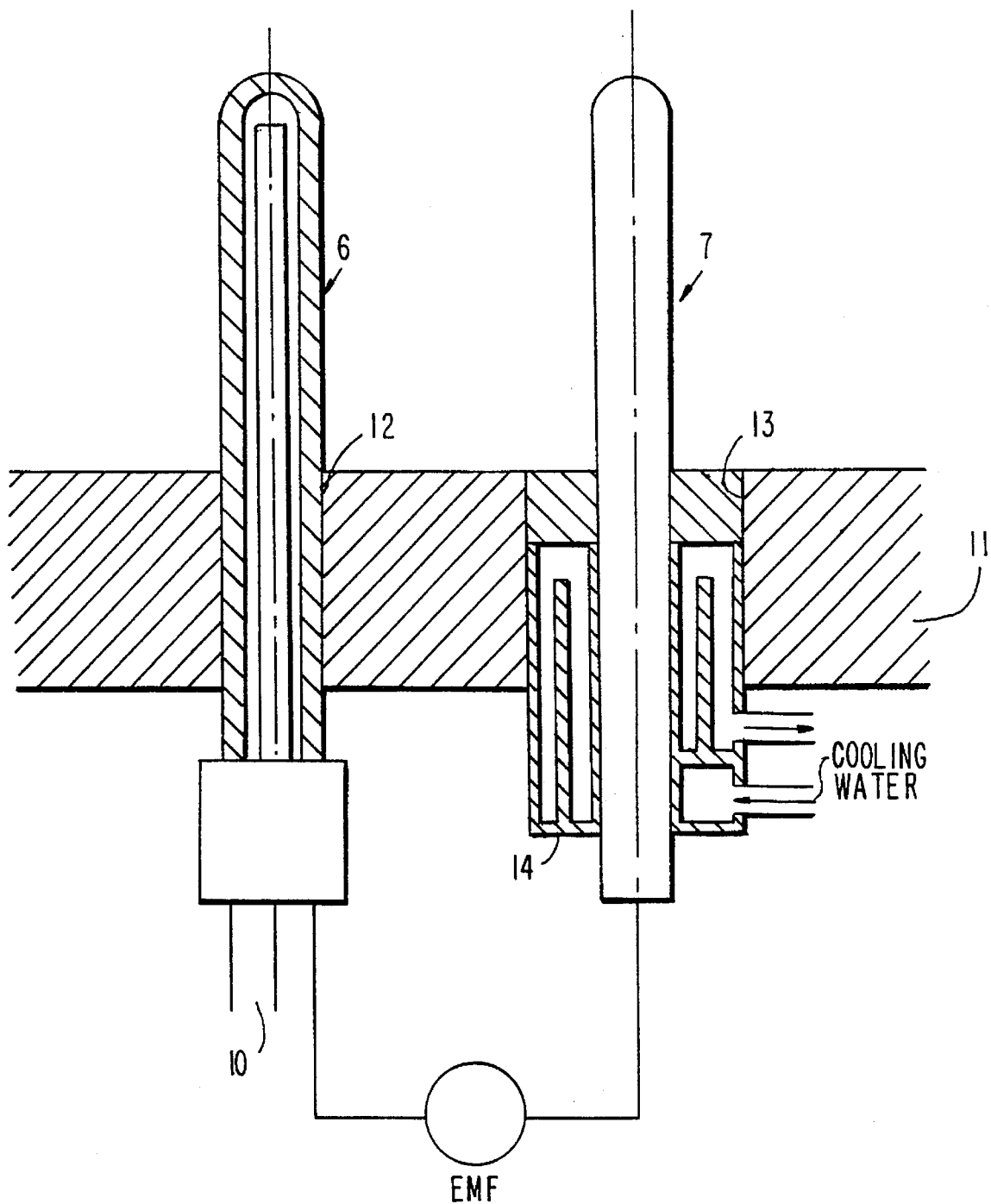
FIG. 2 is a schematic cross-sectional view of a measurement apparatus in which an electrode according to the invention is used as a ground electrode.

An Me/Me$_x$O$_y$ electrode is used as a ground electrode in the glass melt-containing vessel shown in FIG. 2. The arrangement shown in the figure includes a Me/Me$_x$O$_y$—rod 7 and a Pt-counter electrode 6 formed as a pipe closed on one end, both of which project from below through the base 11 of the glass melt-containing vessel. Both electrodes 6,7 are fixed in openings 12, 13 in the furnace base 11 made of fire resistant material and sealed therein. The holder for the Me/Me$_x$O$_y$ electrode 7 is coolable with a cooling fluid. Because of that the reference electrodes can be replaced during operation when the melt is formed in operation. The thermocouple element 10 is arranged in the interior of the platinum electrode 6. The electrical connection of the electrodes 6,7 and the thermocouple elements are made outside the glass melt-containing vessel under the furnace base 11.

While the invention has been illustrated and described as embodied in a reference electrode for electrochemical measurement of the oxygen partial pressure in an ionic melt, it is not intended to be limited to the details shown, since various modifications and structural changes may be made without deviating in any way from the spirit of the invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. Method for electrochemical determination of oxygen partial pressure in a glass melt, said method comprising the steps of:

a) immersing a pure platinum electrode and a reference electrode in the glass melt, said reference electrode being a metal/metal oxide electrode consisting of an electrode body made of a metal selected from the group consisting of Mo, W, Hf, Nb and Ta and alloys thereof and a layer of an oxide of said metal on said electrode body;

b) measuring a potential across said reference electrode and said pure platinum electrode immersed in said glass melt to obtain a measured potential characteristic of said oxygen partial pressure in said glass melt;

c) obtaining a calibration curve relating said potential across said reference electrode and said pure platinum electrode to the oxygen partial pressure in the glass melt as a function of temperature, wherein said obtaining of said calibration curve comprises immersing a zirconium dioxide electrode in said glass melt and measuring a potential difference between said metal/metal oxide electrode and said Zirconium dioxide electrode at a plurality of temperatures; and d) obtaining said oxygen partial pressure in said glass melt from said measured potential and said calibration curve.

2. The method as defined in claim 1, wherein glass melt is an oxidic glass melt, and further comprising providing said Zirconium dioxide electrode with a platinum interior conductor and an interior oxygen rinse at a pressure of 1 bar and measuring said temperatures with a thermocouple.

3. A method for electrochemical determination of oxygen partial pressure in a glass melt, said method comprising the steps of:

a) immersing a pure platinum electrode and a reference electrode in the glass melt, said reference electrode consisting of a metal/metal oxide electrode consisting of an electrode body made of a metal selected from the group consisting of Mo, W, Hf, Nb and Ta and alloys thereof and a layer of an oxide of said metal on said electrode body;

b) measuring a potential across said reference electrode and said pure platinum electrode immersed in said oxidic glass melt to obtain a measured potential characteristic of said oxygen partial pressure in the melt;

c) obtaining a calibration curve relating said potential across said reference electrode and said pure platinum electrode to the oxygen partial pressure in the glass melt as a function of temperature, wherein said obtaining said calibration curve comprises calculating said calibration curve from thermodynamic data for said metal and said metal oxide of said metal; and d) obtaining said oxygen partial pressure in said glass melt from said measured potential and said calibration curve.

4. The method as defined in claim 3, wherein only relative values of said oxygen partial pressure in said glass melt are obtained, and further comprising calculating said relative values of said oxygen partial pressure in the glass melt from calculated relative values of said oxygen partial pressure at the $Me_xO_y$ phase boundary determined from the following thermodynamic relationship:

$$\delta \log pO_2(Me/Me_xO_y)/\delta(1/T) = -(2/y) \Delta H°/(2.303R)$$

wherein $pO_2(Me/Me_xO_y)$ is said oxygen partial pressure at the $Me_xO_y$ phase boundary, R is the gas constant, T=temperature, °K, and $\Delta H°$ is the metal oxide enthalpy of formation.

5. An apparatus for electrochemical determination of at least relative values of oxygen partial pressure in a glass melt, said apparatus comprising only two electrodes, one of the two electrodes being made of pure platinum and the other of the two electrodes being a metal/metal oxide electrode consisting of an electrode body made of a metal selected from the group consisting of Mo, W, Hf, Nb, Ta and alloys thereof and an oxide layer on said electrode body, said oxide layer consisting of an oxide of said metal, means for holding said two electrodes in said glass melt, a sleeve surrounding a portion of said metal/metal oxide electrode not immersed in said glass melt, an inert gas atmosphere inside said sleeve around said portion and means for measuring an electrochemical potential across said two electrodes to obtain a measured potential characteristic of relative values of the oxygen partial pressure in the glass melt.

6. The apparatus as defined in claim 5, further comprising means for calculating said relative values of said oxygen partial pressure in said glass melt from said measured potential and thermodynamic data for said metal and said oxide of said metal.

7. The apparatus as defined in claim 5, wherein said metal is said Mo and said oxide is $MoO_2$.

8. The apparatus as defined in claim 7, wherein said electrode body is in the form of a rod.

9. The apparatus as defined in claim 5, further comprising thermocouple means for measuring a temperature of said glass melt.

10. An apparatus for electrochemical determination of oxygen partial pressure in a glass melt, said apparatus comprising a pure platinum electrode, a Zirconium dioxide electrode including an internal platinum wire and an internal oxygen flush at a set pressure, a metal/metal oxide electrode selected from the group consisting of $Mo/MoO_2$, $W/WO_2$, $Hf/HfO_2$, $Nb/NbO$ and $Ta/Ta_2O_5$ electrodes, means for immersing said platinum, Zirconium oxide and said metal/metal oxide electrodes in said glass melt, a sleeve surrounding a portion of said metal/metal oxide electrode not immersed in said glass melt and an inert gas atmosphere inside said sleeve around said portion, means for measuring an electrochemical potential across said Zirconium dioxide electrode and said metal/metal oxide electrode to calibrate said metal/metal oxide electrode, and means for measuring an electrochemical potential across said metal/metal oxide electrode and said pure platinum electrode to obtain a measured potential characteristic of an oxygen partial pressure in said glass melt, wherein said metal/metal oxide electrode consists of an electrode body made of a metal selected from the group consisting of Mo, W, Hf, Nb and Ta and alloys thereof and a layer of an oxide of said metal on said electrode body, said layer being formed by a method including immersing said electrode body in said glass melt.

11. The apparatus as defined in claim 10, wherein said metal is said Mo and said oxide is $MoO_2$.

12. The apparatus as defined in claim 11, wherein said electrode body is in the form of a rod.

13. The apparatus as defined in claim 10, further comprising thermocouple means for measuring a temperature of said glass melt.

* * * * *